(12) United States Patent
Revesz et al.

(10) Patent No.: US 7,581,876 B2
(45) Date of Patent: Sep. 1, 2009

(54) DUAL ENERGY SOURCE LOSS-ON-DRYING INSTRUMENT

(75) Inventors: Robert N. Revesz, Monroe, NC (US); Michael J. Collins, Sr., Charlotte, NC (US)

(73) Assignee: CEM Corporation, Matthews, NC (US)

( * ) Notice: Subject to any disclaimer, the term of this patent is extended or adjusted under 35 U.S.C. 154(b) by 152 days.

(21) Appl. No.: 11/457,798

(22) Filed: Jul. 15, 2006

(65) Prior Publication Data

US 2008/0013592 A1   Jan. 17, 2008

(51) Int. Cl.
G01N 5/02 (2006.01)
G01N 25/56 (2006.01)
G01J 5/00 (2006.01)
H05B 6/64 (2006.01)
G01K 7/00 (2006.01)
G01K 13/00 (2006.01)
G01G 9/00 (2006.01)

(52) U.S. Cl. .......................... 374/14; 374/45; 374/121; 374/122; 374/179; 374/142; 73/73; 73/76; 219/708; 219/680; 219/756; 702/130; 702/134; 702/173

(58) Field of Classification Search .................. 374/14, 374/45, 122, 179, 121; 73/73, 76; 702/130, 702/134, 173; 219/756, 680, 708
See application file for complete search history.

(56) References Cited

U.S. PATENT DOCUMENTS 3,909,598 A    9/1975   Collins et al.

(Continued)

FOREIGN PATENT DOCUMENTS

DE   34 11 495 A1   10/1985

(Continued)

OTHER PUBLICATIONS

European Search Report of foreign counterpart application No. EP 07111135.5, mailed Nov. 27, 2007, 9 pages.

(Continued)

*Primary Examiner*—Gail Verbitsky
*Assistant Examiner*—Mirellys Jagan
(74) *Attorney, Agent, or Firm*—Summa, Addition & Ashe, P.A.

(57) ABSTRACT

An instrument and associated method are disclosed for the loss-on-drying determination of the volatile content of a wide variety of samples. The instrument includes a cavity in which a sample for which the volatile content is to be determined can be placed, a first source for introducing microwaves into the cavity that have frequencies substantially other than infrared frequencies, a second source for introducing radiant heat into the cavity at frequencies different from the frequencies introduced by the first source, an analytical balance for measuring the weight of a sample while the sample is in the cavity and on the balance, a temperature sensor capable of measuring and positioned to measure the temperature of a sample in the cavity and on the balance, and a processor in communication with the temperature sensor and each of the first and second sources for controlling the introduction of the frequencies of microwave and radiant energy into the cavity in response to the temperatures measured by the temperature sensor to control the sample temperature until the microwaves from the first source and the radiant heat from the second source dry the sample sufficiently for the processor to determine the volatile content of the sample based on the weight change of the sample on the balance.

11 Claims, 2 Drawing Sheets

U.S. PATENT DOCUMENTS

| | | | |
|---|---|---|---|
| 4,291,775 A | | 9/1981 | Collins |
| 4,554,132 A | | 11/1985 | Collins |
| 4,566,804 A | | 1/1986 | Collins et al. |
| 4,681,996 A | | 7/1987 | Collins et al. |
| 4,751,356 A | | 6/1988 | Fukuda et al. |
| 4,807,633 A | | 2/1989 | Fry |
| 4,889,201 A | * | 12/1989 | Oldendorf et al. ........ 177/25.14 |
| 4,964,734 A | * | 10/1990 | Yoshida et al. ................ 374/14 |
| 5,983,711 A | * | 11/1999 | Pappas et al. ................... 73/76 |
| 6,084,226 A | | 7/2000 | Greene et al. |
| 6,092,924 A | * | 7/2000 | Scalese et al. ................ 374/14 |
| 6,227,041 B1 | | 5/2001 | Collins et al. |
| 6,268,570 B1 | | 7/2001 | McLendon et al. |
| 6,302,577 B1 | | 10/2001 | Jennings et al. |
| 6,394,647 B1 | | 5/2002 | Allmendinger et al. |
| 6,566,637 B1 | | 5/2003 | Revesz et al. |
| 6,787,362 B2 | | 9/2004 | Collins et al. |
| 7,100,428 B1 | * | 9/2006 | Dziki ............................ 73/73 |
| 2007/0199370 A1 | * | 8/2007 | Diedrich et al. ................ 73/73 |

FOREIGN PATENT DOCUMENTS

| | | |
|---|---|---|
| DE | 4442078 | 5/1996 |
| JP | 10038783 A | 2/1998 |
| WO | WO 00 16067 A | 3/2000 |
| WO | WO 2007 045510 A | 4/2007 |

OTHER PUBLICATIONS

Mettler Toledo, "Methods of moisture content determination," Application Brochure, 2002, Retrieved from Internet Oct. 30, 2007 at URL:http://www.northshorecare.com/moisture-methods.pdf, pp. 1-67.

Robens et al., "Graviemetric measurement of water vapour sorption, moisture and dry mass," Journal of Thermal Analysis and Calorimetry, Kluwer Academic Publishers, DO, vol. 76, No. 2, May 1, 2004, pp. 639-646.

Tireki et al., "Production of bread crumbs by infrared-assisted microwave drying," European Food Research and Technology, Jan. 1, 2006, vol. 222, No. 1-2, pp. 8-14.

* cited by examiner

DUAL ENERGY SOURCE LOSS-ON-DRYING INSTRUMENT

BACKGROUND

The present invention relates generally to the field of microwave-assisted chemistry techniques, and in particular relates to instrumentation and techniques for conducting loss-on-drying analyses and calculations for a wide variety of materials.

Measuring the sample volatile content (which in many cases is the moisture content) is a frequent and repetitive chore in many analytical laboratories. For example, in a manufacturing setting, the measurement of sample volatile content may be an important step in a quality control procedure. If the time for conducting the analysis is long, then poor quality samples may not be detected for several hours or days. In this circumstance, the manufacturing facility may have continued producing the lower quality product throughout the time necessary for conducting the test. Accordingly, a large quantity of poor quality material may have been produced before the quality problem was discovered. Such a delay often leads to cost overruns and manufacturing delays, as the poor quality product may require disposal and the manufacturing process must begin again.

In its simplest form, determining volatile or moisture content consists of weighing a representative sample of material, drying the material, then re-weighing the material to ascertain the losses on drying and, consequently, the initial volatile content of the sample. Convective, hot-air ovens, which are often used for this task, can be relatively slow to bring the sample to "oven-dry" equilibrium. Such devices can also be expensive to operate as they inefficiently consume energy. These problems lessen the utility of hot-air devices for volatile analysis.

Drying certain substances using microwave energy to determine volatile or moisture content is generally convenient and precise. The term "microwaves" refers to that portion of the electromagnetic spectrum between about 300 and 300,000 megahertz (MHz) with wavelengths of between about one millimeter (1 mm) and one meter (1 m). These are, of course, arbitrary boundaries, but help quantify microwaves as falling below the frequencies of infrared (IR) radiation and above those referred to as radio frequencies. Similarly, given the well-established inverse relationship between frequency and wavelength, microwaves have longer wavelengths than infrared radiation, but shorter than radio frequency wavelengths. Additionally, a microwave instrument incorporating a micro-processor can monitor the drying curve (weight loss vs. time) of a sample and can predict the final dried weight (and thus the original moisture content) based on an initial portion of the drying curve. Such analyses may be conducted in about two to three minutes for samples that contain free water.

More importantly, microwave drying to measure moisture content is usually faster than equivalent hot-air methods. As in hot-air techniques, however, certain substances tend to burn, rather than merely become dry, when microwave power is applied to them. Stated differently, the rapid manner in which microwaves tend to interact with certain materials, which is an obvious advantage in some circumstances, can cause secondary heating of other materials that is disadvantageous (at lest for volatile or moisture measurement purposes). Certain food products such as cheese are exemplary (although certainly not limiting) of materials that tend to burn rather than dry when exposed to microwaves.

Additionally, microwaves interact with materials in a fashion known as "coupling," i.e., the response of the materials ("the load") to the microwave radiation. Some materials do not couple well with microwave energy, making drying or other volatile removal techniques difficult or imprecise. Other materials couple well when their moisture content, or content of other microwave-responsive materials (e.g., alcohols and other polar solvents), is high. As they dry under the influence of microwaves, however, they couple less and less effectively; i.e., the load changes. As a result, the effect of the microwaves on the sample becomes less satisfactory and more difficult to control. In turn, the sample can tend to burn rather than dry, or degrade in some other undesired fashion. Both circumstances, of course, tend to produce unsatisfactory results.

As another factor, volatiles, such as "loose" water (i.e., not bound to any compound or crystal) respond quickly to microwave radiation, but "bound" water (i.e., water of hydration in compounds such as sodium carbonate monohydrate, $Na_2CO_3.H_2O$) and nonpolar volatiles (e.g., low molecular weight hydrocarbons and related compounds) are typically unresponsive to microwave radiation. Instead, such bound water or other volatiles must be driven off thermally; i.e., by heat conducted from the surroundings.

Thus, microwaves can help remove bound water from a sample when the sample contains other materials that are responsive to microwaves. In such cases, the secondary heat generated in (or by) the microwave-responsive materials can help release bound water. The nature of microwave radiation is such, however, that not all such materials or surroundings may be heated when exposed to microwaves. Thus, loss-on-drying measurements using microwaves are typically less satisfactory for determining bound water than are more conventional heating methods.

In order to take advantage of the speed of microwave coupling for samples that do not readily absorb or couple with microwaves, techniques have been incorporated in which a sample is placed on a material that absorbs microwaves and becomes heated in response to those microwaves (often referred to as a susceptor). U.S. Pat. No. 4,681,996 is an example of one such technique. As set forth therein, the goal is for the thermally-responsive material to conductively heat the sample to release the bound water. Theoretically, a truly synergistic effect should be obtained because the thermally heated material heats the sample to remove bound water while the free water responds to, and is removed by, the direct effect of the microwaves.

In such susceptor techniques, when non-polar solvents are present with bound or free water in material to be analyzed for volatiles, they are likewise volatilized by the thermal heat generated by the susceptor, while the free water (which may have been thermally released from a bound form), is vaporized by the microwave radiation. Thus, volatiles may be quickly removed from the sample whether the volatiles are bound water, free water, other polar materials, or non-polar compounds.

Susceptor techniques, however, are less successful in actual practice. As one disadvantage, the necessary susceptors are often self-limiting in temperature response to microwaves, and thus different compositions are required to obtain different desired temperatures.

As a third disadvantage, the predictability of a susceptor's temperature response can be erratic. As known to those familiar with content analysis, certain standardized drying tests are based upon heating a sample to, and maintaining the sample at, a specified temperature for a specified time. The weight loss under such conditions provides useful and desired information, provided the test is run under the specified conditions.

Thus, absent such temperature control, microwave techniques may be less attractive for such standardized protocols.

As another disadvantage, the susceptor may tend to heat the sample unevenly. For example, in many circumstances, the portion of the sample in direct contact with the susceptor may become warmer than portions of the sample that are more remote. Such uneven temperatures may lead to incomplete removal of bound moisture as well as inaccurate loss-on-drying analyses.

Bound water may be removed in some circumstances by applying infrared radiation to a sample. Infrared radiation succeeds in driving off bound water (as well as any free water) by raising the temperature of the sample to an extent that overcomes the activation energy of the water-molecule bond. Infrared drying is also faster than oven drying for many samples. Nevertheless, infrared radiation tends to heat moisture-containing samples relatively slowly as compared to microwaves. Furthermore, infrared radiation does not couple with materials. Instead it typically heats the surface (or near surface) of the material following which the heat conducts inwardly; and typically takes time to do so. Infrared radiation will, however, heat almost all materials to some extent, and thus it offers advantages for materials that do not couple with microwaves.

Merely using two devices (e.g., one microwave and one infrared) to remove the two types of volatiles does not provide a satisfactory solution to the problem because moving the sample between devices typically results in at least some cooling, some loss of time (efficiency), the potential to regain moisture (under principles of physical and chemical equilibrium), and an increase in the experimental uncertainty (accuracy and precision) of the resulting measurement. Furthermore, if a sample is moved from a first balance in a microwave cavity to a second (separate) balance exposed to infrared radiation, the tare on the first balance would be meaningless with respect to the use of the second balance.

Accordingly, a need exists for loss-on-drying instrumentation and techniques that minimize or eliminate the disadvantages of prior methods or devices with respect to a wider variety of sample materials.

SUMMARY

The invention is an instrument and associated method for determining the volatile content of a sample while monitoring or controlling the sample temperature. The instrument includes a cavity in which a sample for which the volatile content is to be determined can be placed, a first source for introducing microwaves into the cavity that have frequencies substantially other than infrared frequencies, a second source for introducing radiant heat into the cavity at frequencies different from the frequencies introduced by the first source, an analytical balance for measuring the weight of a sample while the sample is in the cavity and on the balance, a temperature sensor capable of measuring and positioned to measure the temperature of a sample in the cavity and on the balance, and a processor in communication with the temperature sensor and each of the first and second sources for controlling the introduction of the frequencies of microwave and radiant energy into the cavity in response to the temperatures measured by the temperature sensor to control the sample temperature until the microwaves from the first source and the radiant heat from the second source dry the sample sufficiently for the processor to determine the volatile content of the sample based on the weight change of the sample on the balance.

The foregoing and other aspects and embodiments of the invention will become clearer based on the following detailed description taken in conjunction with the accompanying drawings.

DETAILED DESCRIPTION

The present invention is an instrument and associated method for determining the volatile content of a wide variety of samples, typically samples that contain both "free" and "bound" water (moisture) or other non-polar volatile materials while monitoring or controlling the sample temperature to prevent burning or decomposition of the sample other than loss of moisture. The invention takes advantage of the speed capabilities of microwave drying with respect to free water and the favorable characteristics of radiant energy (increased temperature) with respect to the removal of bound water without limiting the process to the slower of either step (technique).

Figure 1:
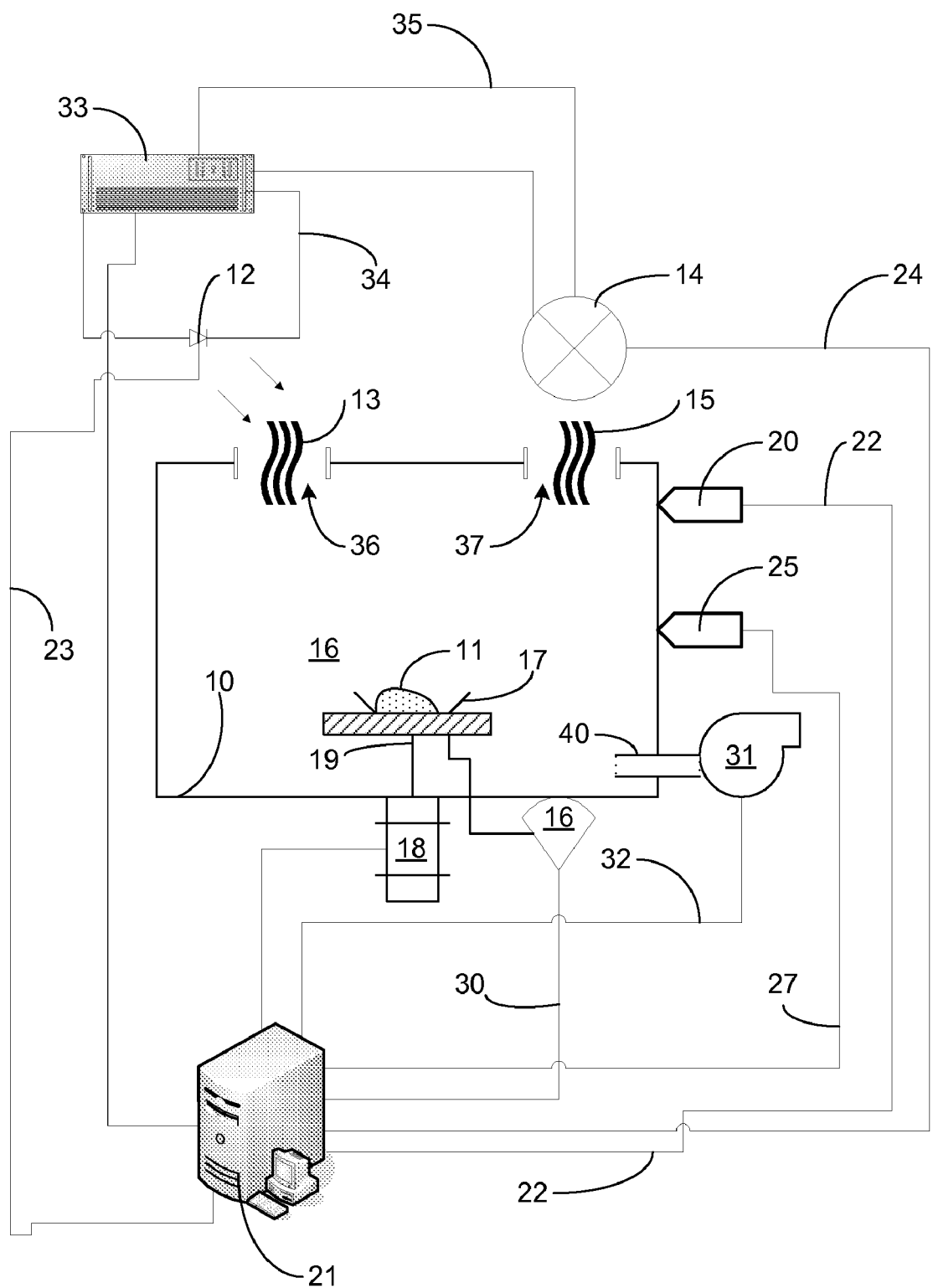
FIG. 1 is a schematic diagram of an instrument according to the present invention.

FIG. 1 is a schematic diagram of an instrument according to the present invention. The instrument includes a cavity illustrated as the rectangle 10. A sample 11 for which the volatile content is to be determined is typically positioned in the cavity 10. A source schematically illustrated as the diode 12 introduces microwaves symbolically illustrated at 13 into the cavity 10. The source 12 is typically selected from the group consisting of magnetrons, klystrons, and IMPATT diode devices, each of which can produce electromagnetic radiation in the microwave frequencies. Each is selected in various circumstances based on considerations such as size or cost that are important to the user and otherwise consistent with the remainder of the instrument. Each is likewise well-understood in the art and need not be discussed in detail herein.

A second source illustrated as the lamp 14 introduces radiant heat symbolically illustrated at 15 into the cavity 10 and directed toward the sample 11 at frequencies that are different from the microwave frequencies introduced by the first source 12. An analytical balance 16 measures the weight of the sample 11 which is typically positioned on a pan 17 (functionally connected to the balance 16) or other holder while the sample 11 is in the cavity 10. In many embodiments, a motor 18 and shaft 19 rotate the sample at a relatively slow speed to encourage more uniform heating and drying. Commonly assigned U.S. Pat. No. 6,302,577 describes an exemplary balance arrangement, and the contents of this patent are incorporated entirely herein by reference.

At least one temperature sensor 20 is positioned to measure the temperature of the sample 11 in the cavity 10 while the sample 11 is on the balance 16. A processor 21 is in communication with the temperature sensor 20 through the signal line 22. In this regards, and although FIG. 1 illustrates the various components as being connected by lines which typically symbolize electrical wiring, it will be understood that one or more of the components can be in wireless communication with each other using standards such as 802.11 ("WiFi").

The processor 21 is also in communication with the microwave source 12 through the signal line 23 and with the lamp 14 through the signal line 24. This enables the processor 21 to control the introduction of both microwave frequencies 13 and radiant heat 15 into the cavity 10 in response to the temperature measured by the sensor 20. This in turn helps to control the temperature of the sample 11 until the microwaves 13 from the microwave source 12 and the radiant heat 15 from the lamp 14 dry the sample sufficiently for the processor 21 to determine the volatile content of the sample 11 based upon the weight change.

The basic principles of control circuits are well understood in the electrical engineering arts and will not be described in detail herein. Appropriate and representative descriptions are set forth in widely available sources such as Dorf, THE ELECTRICAL ENGINEERING HANDBOOK, Second Edition, CRC Press (1997). Similarly, the basic characteristics of microwave instrumentation are well understood in the art, and representative commercial and patented examples are available from the assignee of the present invention, CEM Corporation, Matthews, N.C., USA and other sources. Infrared heating techniques, standing alone, are likewise well understood in the art and representative commercial infrared instruments are likewise widely available in the marketplace.

The speed and capacity of the processor 21 can be selected as desired, but will typically have a capability similar to that of a desktop personal computer. The term "processor" is used in a relatively broad sense herein and can include the appropriate memory and bus components of a personal computer in addition to the processor chip itself.

In one embodiment, the temperature sensor 20 is an optical pyrometer or equivalent photosensor that measures the temperature of the sample 11 rather than the temperature of the cavity or the ambient surroundings. Infrared photodetectors can be at least partially useful for this purpose because they are non-invasive; i.e., they do not touch the sample and instead determine the sample temperature by measuring the IR frequencies emitted by the sample. Other common temperature measurement devices include thermometers (which are non-electrical in nature and operation) thermocouples, thermistors, and resistance thermometers. Each of these works in well understood fashion.

The radiant energy 15 provided by the lamp 14 will, however, often include infrared frequencies that can flood the IR detector when the lamp is in operation and thus prevent the IR detector from distinguishing between IR frequencies emitted by the sample and those emitted by the lamp. Therefore, in other embodiments the instrument can include a second temperature sensor 25 that measures characteristics other than infrared radiation to thereby measure temperature in the presence of infrared radiation from the lamp. The second temperature sensor 25 can be a thermocouple or similar device provided that it is arranged in a manner that does not interfere with the weighing function of the balance 16. The second temperature detector 25 is in communication with the processor 21 through the line (or equivalent) 27.

FIG. 1 also illustrates that the processor 21 is in communication through the line 30 with the analytical balance 16 in order to obtain weight information from the balance 16 and to optionally control the introduction of microwave energy 13 or radiant energy 15 to the sample in response to the measured weight.

Similarly, if desired the instrument can include a fan 31 for removing volatiles from the cavity 10 as the sample 11 is being heated or for generally providing movement of heated air from the cavity 10 in order to help moderate the temperature. The fan 31 can include a variable speed mechanism and can communicate with the processor 21 through the line 32 in order to control the fan speed and airflow in response to the processor 21 and in turn from additional input such as the temperature measured by either of the sensors 20, 25 or the weight measured by the balance 16.

The lamp 14 can be selected from among various sources that provide desired radiant energy including infrared lamps, quartz heaters, incandescent lamps, metal heating elements, and halogen lamps. These are nevertheless exemplary of the invention rather than limiting. The microwave source 12 and the lamp 14 can be powered by one or more power supplies one of which is schematically illustrated at 33. Although only one power supply 33 is illustrated, separate power supplies can be included for each source 12, 14 if desired. With respect to microwave radiation, the power supply 33 can be a switching power supply as described in commonly assigned and incorporated U.S. Pat. No. 6,084,226. The power supply 33 and the microwave source 12 form part of an appropriate circuit 34 which can be otherwise conventional and need not be described further herein. Similarly, the power supply 33 and the lamp 14 form respective parts of a circuit 35 which can likewise be conventional provided it is consistent with the other operating features of the instrument. An exemplary lamp is a halogen projector lamp, such as the 82 volt, 360 watt lamps (and similar lamps) available from Ushio America, Inc. (5440 Cerritos Ave Cypress, Calif. 90630) or the 120 volt, 250 watt lamps from SEC, 4901 Gregg Road, Pico Rivera, Calif. 90660.

FIG. 10 also schematically illustrates a waveguide illustrated as the opening 36 in the cavity 10. It will be understood that waveguides and other openings in the cavity 10 must be of a size and shape that, in most circumstances, precludes microwaves from escaping from the cavity 10. The relationship of the diameter and length of such waveguides and attenuators to the propagated microwave frequency is well understood in the art and can be selected by persons of ordinary skill in the art without undue experimentation.

Similarly, the radiant heat source 14 is either adjacent to, or in optical or thermal communication with, an appropriate window or opening 37. The term opening is used in a functional sense with respect to radiant energy and thus can include an optical window that is transparent to the desired frequencies and need not represent a physical opening in the cavity 10. The size, shape and materials for the opening 37 are in most circumstances consistent with the goal of precluding microwaves from escaping from the cavity 10 as previously described with respect to the waveguide 36.

FIG. 1 illustrates a third opening shown as the vent 40 from the cavity to the fan 31. Such an exhaust opening or event will likewise share (in most circumstances) the characteristics of precluding the transmission of microwave energy.

Figure 2:
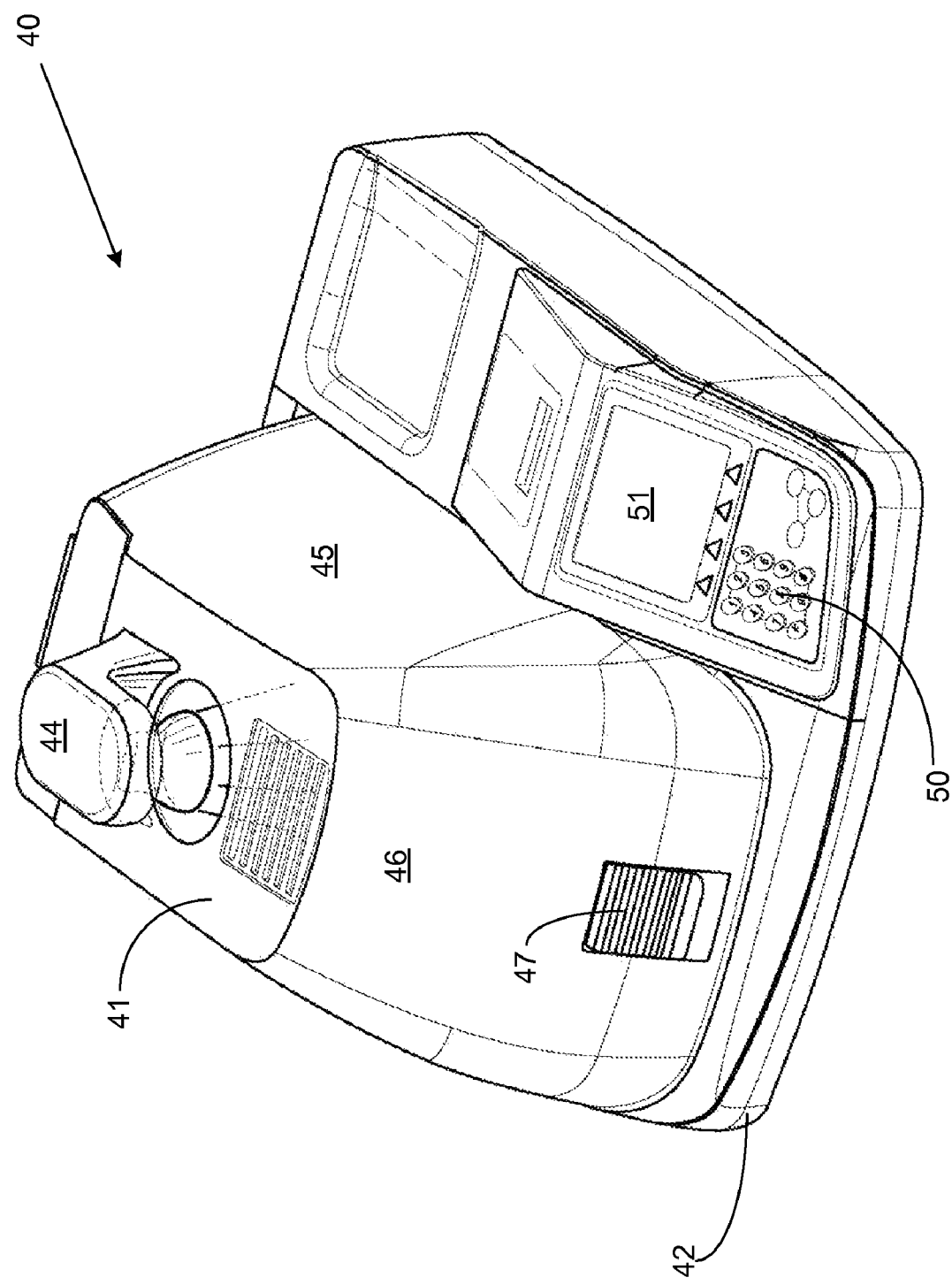
FIG. 2 is a perspective view of an instrument according to the present invention.

FIG. 2 is a perspective view of an instrument 40 according to the present invention. In this embodiment, the instrument 40 includes an upper housing portion 41 and a base portion 42. The housing 41 and the base 42 together enclose the cavity (not shown in FIG. 2) in a manner analogous to the cavity described in commonly assigned U.S. Pat. No. 6,566,637, the contents of which are incorporated entirely herein by reference. In turn, the SMART™ instruments commercially available from CEM Corporation, the assignee herein, incorporate many of the features described in U.S. Pat. No. 6,566,637.

In this embodiment, the lamp (designated at 14 consistent with FIG. 1) is positioned on a top surface 43 of the upper housing 41. In this position, the lamp 14 can direct infrared radiation (and typically some visible frequencies as well) into the cavity in the manner illustrated schematically in FIG. 1. A fixture 44 holds the lamp 14 in position and supplies it with the appropriate electrical and physical connections. These can be otherwise conventional and are well understood in this art and thus will not be described in detail herein.

Because the lamp 14 serves to direct heat radiation, including infrared radiation, into the cavity, its illustrated position in FIG. 2 is exemplary rather than limiting. Thus, the lamp 14 could be positioned on one of the sidewalls 45 or 46 of the housing 41, or could even project from the base portion 42 in some other arrangement.

FIG. 2 also illustrates that the housing 41 includes the latch 47 that can be used to physically open the housing, which is typically hinged towards the rear.

FIG. 2 also illustrates a keyboard or alphanumerical pad 50, which can be used to provide input to the processor, as well as a display 51 that can visibly illustrate both input and output; e.g., the weight percentage of the sample as calculated by the processor. Such input and output elements are well understood in the relevant art and need not be described in detail. The keypad 50 can be mechanically-based or touch-based among other choices. Similarly, the display 51 can be based on any size-function-cost appropriate technology including cathode ray tubes (CRT's) light emitting diodes (LEDs) or liquid crystal displays (LCDs). Such displays are well-understood and are becoming conventional in small sizes; e.g. the color displays on typical cellular telephones.

In another aspect, the invention is a method for determining the moisture (or volatile) content of a sample that contains both free and bound water, and potentially polar volatiles and nonpolar volatiles. In this aspect, the invention comprises the steps of positioning a sample to be analyzed on a balance in a microwave cavity, applying microwave energy that has frequencies substantially other than the infrared frequencies to the sample to heat the sample and remove free moisture (and any polar volatiles) from the sample, applying radiant energy that has frequencies substantially other than microwave frequencies to the sample to heat the sample and remove bound moisture (and potentially any nonpolar volatiles) from the sample, monitoring (measuring) the weight of the sample during the application of microwave and radiant energy, monitoring the temperature of the sample during the application of both microwave and radiant energy, and moderating the microwave and radiant energy applied to the sample in response to the measured temperature in a manner that maintains the temperature of the sample below temperatures at which the sample would burn while continuing to measure the weight of the sample with the analytical balance and as the sample dries. It will be understood, of course that the method does not require that both free water and polar volatiles be present in the sample, but rather that if either or both are present, the method can remove them. The same is true for bound water or nonpolar volatiles; either or both can be present, and if so, the method can remove them.

In particular, the method comprises measuring the weight of the sample before applying the microwave energy to the sample, measuring the weight of the sample after removing bound water, and calculating the moisture (or other volatile) content of the sample based upon the measured weights.

The steps of applying microwave energy and radiant energy can be conducted concurrently for at least some period of time. Alternatively the microwave energy and the radiant energy can be applied consecutively. Most typically, and in order to take advantage of the speed of microwave coupling, the microwave energy is applied either prior to or concurrently with the step of applying the radiant energy. Most typically, the microwave energy is applied until the weight change indicates that the free moisture has been substantially removed. At this point, the coupling advantages of microwaves no longer apply (or are very small) and the bound water and other nonpolar volatile materials can be removed most efficiently by applying the radiant energy.

Similarly, the method can include measuring the initial temperature prior to applying either of the microwave energy or the radiant energy to the sample.

In typical embodiments, the weight of the sample is measured continuously as the microwave energy and the radiant energy are being applied. The temperature is typically measured continuously as well.

In some cases, and depending upon the sample materials, the loss of total moisture can be predicted based upon the rate of moisture loss during the microwave and radiant energy steps; i.e., based on information obtained before the sample becomes totally dry.

In the method, the step of moderating the microwave energy can comprise moderating the microwave power produced by the source, or by moderating the passage of microwaves between the source and the cavity. Similarly, the radiant energy can be moderated by moderating the energy produced by the source or by moderating the transmission of the radiant energy between the source 14 and the sample 11.

For the sake of efficiency, the method can include using the processor to turn off the microwave energy and the radiant energy when the weight change (or lack thereof) indicates that the sample has dried.

Alternatively, the processor can calculate the difference in the rate of weight loss as microwaves are being applied to recognize that the free water has been driven off and that the microwave source should be replaced with the radiant heat source for the remainder of the drying process.

The invention accordingly takes advantage of the speed capabilities of microwave drying with respect to free water and the favorable characteristics of radiant energy (increased temperature) with respect to the removal of bound water without limiting the process to the slower of either step (technique) in either circumstance.

In the drawing and specification, there has been set forth preferred embodiments of the invention, and although specific terms have been employed, they are used in a generic and descriptive sense only and not for purposes of limitation, the scope of the invention being defined in the claims.

The invention claimed is:

1. An instrument for determining the volatile content of a sample while monitoring or controlling the sample temperature, the instrument comprising:
   a cavity in which a sample for which the volatile content is to be determined can be placed;
   a first source of electromagnetic radiation for introducing microwaves into said cavity that have frequencies substantially other than infrared frequencies;
   a second source of electromagnetic radiation for introducing electromagnetic radiation into said cavity at frequencies different from the microwave frequencies introduced by said first source;
   an analytical balance for measuring the weight of a sample while the sample is in said cavity and on said balance; and
   a processor in communication with said balance and each of said first and second sources for controlling the introduction of said frequencies from said first and second sources into said cavity in response to said balance until the microwaves from said first source and the frequencies from said second source dry the sample sufficiently for said processor to determine the volatile content of the sample based on the weight change of the sample on said balance.

2. A volatile content determining instrument according to claim 1 wherein said a first source for introducing microwaves is selected from the group consisting of magnetrons, klystrons, and solid state devices for generating microwaves.

3. A volatile content determining instrument according to claim 1 further comprising a waveguide for directing microwaves from said first source to said cavity.

4. A volatile content determining instrument according to claim 1 wherein said second source comprises a source of infrared radiation having enough power to heat the sample.

5. A volatile content determining instrument according to claim 1 wherein said second source is selected from the group consisting of infrared lamps, quartz heaters, incandescent lamps, metal heating elements, and halogen lamps.

6. A volatile content determining instrument according to claim 1 and further comprising an exhaust fan for removing volatiles from said cavity as the sample is being heated therein.

7. A volatile content determining instrument according to claim 6 wherein:
   said exhaust fan is a variable-speed exhaust fan; and
   said processor is in communication with said fan for controlling the speed of said fan in response to said temperature sensor and said analytical balance.

8. A volatile content determining instrument according to claim 1 further comprising:
   a temperature sensor capable of measuring and positioned to measure the temperature of a sample in said cavity and on said balance; and wherein
   said temperature sensor is in communication with said processor for controlling the introduction of said frequencies from said first and second sources into said cavity in response to temperatures measured by said temperature sensor to thereby control the sample temperature.

9. A volatile content determining instrument according to claim 8 wherein said temperature sensor is a thermocouple temperature sensor.

10. A volatile content determining instrument according to claim 8 wherein said temperature sensor comprises an infrared photosensor that measures the temperature of the sample rather than the temperature of the cavity or the ambient surroundings.

11. An instrument according to claim 10 further comprising a second temperature sensor that measures characteristics other than infrared radiation to thereby measure temperature in the presence of infrared radiation that does not represent the temperature of the sample.

* * * * *